(12) United States Patent
Babaev

(10) Patent No.: US 7,901,388 B2
(45) Date of Patent: *Mar. 8, 2011

(54) METHOD OF TREATING WOUNDS BY CREATING A THERAPEUTIC SOLUTION WITH ULTRASONIC WAVES

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 376 days.

This patent is subject to a terminal disclaimer.

(21) Appl. No.: 11/777,986

(22) Filed: Jul. 13, 2007

(65) Prior Publication Data

US 2009/0018491 A1    Jan. 15, 2009

(51) Int. Cl.
*A61M 35/00*    (2006.01)
(52) U.S. Cl. ........................................................ 604/290
(58) Field of Classification Search ................ 604/22, 604/296, 24, 289, 290, 87, 310, 82, 500, 604/518; 239/102.2, 102.1; 366/114, 108, 366/111, 113; 128/200.16
See application file for complete search history.

(56) References Cited

U.S. PATENT DOCUMENTS

| | | | |
|---|---|---|---|
| 3,970,250 A | 7/1976 | Drews | |
| 4,153,201 A | 5/1979 | Berger et al. | |
| 4,402,458 A | 9/1983 | Lierke et al. | |
| 4,469,974 A | 9/1984 | Speranza | |
| 4,507,285 A | 3/1985 | Kuhme | |
| 4,684,328 A | 8/1987 | Murphy | |
| 4,715,353 A | 12/1987 | Koike et al. | |
| 4,834,124 A | 5/1989 | Honda | |
| 4,850,534 A | 7/1989 | Takahashi et al. | |
| 4,875,473 A | 10/1989 | Alvarez | |
| 4,909,244 A | 3/1990 | Quarfoot et al. | |
| 5,000,746 A | 3/1991 | Meiss | |
| 5,336,534 A | 8/1994 | Nakajima et al. | |
| 5,522,794 A | 6/1996 | Ewall | |
| 5,578,022 A | 11/1996 | Scherson et al. | |
| 5,597,292 A | 1/1997 | Rhee et al. | |
| 5,788,682 A | 8/1998 | Maget | |
| 5,792,090 A | 8/1998 | Ladin | |
| 5,855,570 A | 1/1999 | Scherson et al. | |
| 6,010,316 A * | 1/2000 | Haller et al. ................... | 417/322 |
| 6,053,424 A | 4/2000 | Gipson et al. | |
| 6,102,298 A | 8/2000 | Bush | |
| 6,187,347 B1 | 2/2001 | Patterson et al. | |
| 6,234,765 B1 | 5/2001 | Deak | |

(Continued)

FOREIGN PATENT DOCUMENTS

EP    0416106 A1    3/1991

(Continued)

OTHER PUBLICATIONS

De Royal, Jetox-ND Brochure, 2004, Powell, Tennessee, U.S.A.

*Primary Examiner* — Theodore J Stigell

(57) ABSTRACT

A method of treating areas of the body utilizing ultrasonic vibrations to mix different materials together as to create a therapeutic combination is disclosed. The materials are mixed by passing them through an ultrasound horn vibrating in resonance, having an internal chamber. As the materials pass through the internal chamber, ultrasonic vibrations emanating from and/or echoing off the various walls of the chamber mix the materials into a potentially therapeutic combination. Ultrasonic vibrations emanating from the radiation surface of the horn may be used to spray the created therapeutic combination onto the area of the body to be treated.

20 Claims, 7 Drawing Sheets

U.S. PATENT DOCUMENTS

| | | |
|---|---|---|
| 6,478,754 B1 | 11/2002 | Babaev |
| 6,533,803 B2 | 3/2003 | Babaev |
| 6,568,052 B1 | 5/2003 | Rife et al. |
| 6,569,099 B1 | 5/2003 | Babaev |
| 6,601,581 B1 | 8/2003 | Babaev |
| 6,620,379 B1 | 9/2003 | Piuk et al. |
| 6,623,444 B2 | 9/2003 | Babaev |
| 6,663,554 B2 | 12/2003 | Babaev |
| 6,720,710 B1 | 4/2004 | Wenzel et al. |
| 6,723,064 B2 | 4/2004 | Babaev |
| 6,730,349 B2 | 5/2004 | Schwartz |
| 6,761,729 B2 | 7/2004 | Babaev |
| 6,810,288 B2 | 10/2004 | Joshi |
| 6,811,805 B2 | 11/2004 | Gilliard et al. |
| 6,837,445 B1 | 1/2005 | Tsai |
| 6,883,729 B2 | 4/2005 | Putvinski et al. |
| 6,901,926 B2 * | 6/2005 | Yamamoto et al. ...... 128/200.16 |
| 6,964,647 B1 | 11/2005 | Babaev |
| 2001/0020145 A1 | 9/2001 | Satterfield et al. |
| 2001/0020146 A1 | 9/2001 | Satterfield et al. |
| 2002/0127346 A1 | 9/2002 | Heber |
| 2002/0141964 A1 | 10/2002 | Patterson et al. |
| 2002/0160053 A1 | 10/2002 | Yahagi et al. |
| 2002/0190136 A1 * | 12/2002 | Babaev ...................... 239/102.2 |
| 2003/0098364 A1 | 5/2003 | Jameson |
| 2003/0190367 A1 | 10/2003 | Balding |
| 2003/0199815 A1 * | 10/2003 | Trombley et al. ............... 604/82 |
| 2003/0212357 A1 | 11/2003 | Pace |
| 2003/0223886 A1 | 12/2003 | Keilman |
| 2004/0039375 A1 | 2/2004 | Miyazawa |
| 2004/0045547 A1 | 3/2004 | Yamamoto et al. |
| 2004/0204680 A1 | 10/2004 | Lal et al. |
| 2005/0015024 A1 | 1/2005 | Babaev |
| 2005/0064088 A1 | 3/2005 | Fredrickson |
| 2006/0014732 A1 | 1/2006 | Hofman |
| 2006/0034816 A1 | 2/2006 | Davis et al. |
| 2006/0142684 A1 | 6/2006 | Shanbrom |
| 2007/0051307 A1 | 3/2007 | Babaev |
| 2007/0295832 A1 | 12/2007 | Gibson et al. |
| 2008/0006714 A1 | 1/2008 | McNichols et al. |

FOREIGN PATENT DOCUMENTS

| | | | |
|---|---|---|---|
| JP | 57049720 A | * | 3/1982 |
| WO | 9717933 | | 5/1997 |

* cited by examiner

Diamond 1: Select materials to be mixed to make therapeutic solution

Optional →

Box 3: Place at least one free member within the horn

If Atomization and Mixing Desired

Box 2: Pass selected materials through vibrating horn

Box 5: Leave a gas filled space within the horn

Box 4: Mix materials with ultrasonic vibrations emanating from and/or echoing off internal surfaces of the horn If solution is not sufficiently atomized →

Box 6: Atomize created therapeutic soluion

If solution is sufficiently atomized

Box 7: Spray solution onto an area of the body

Figure 1

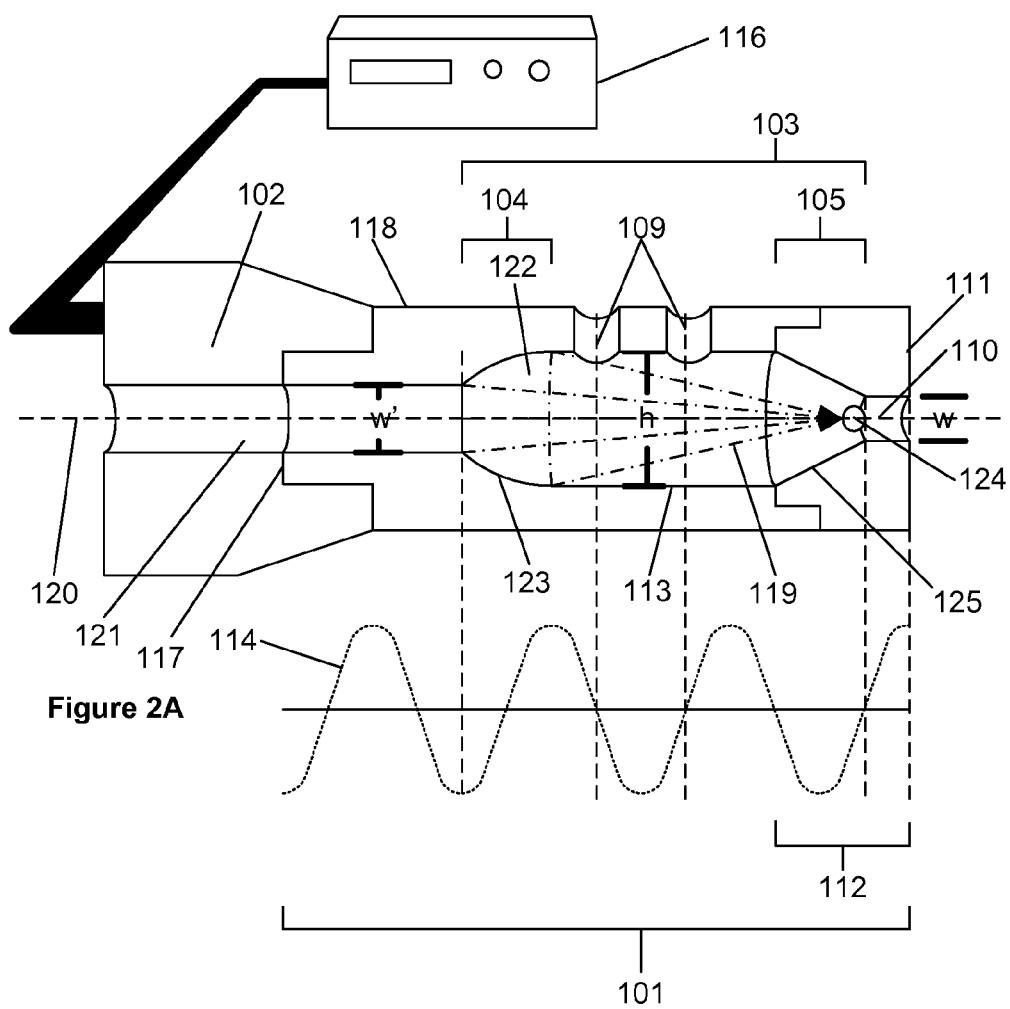

METHOD OF TREATING WOUNDS BY CREATING A THERAPEUTIC SOLUTION WITH ULTRASONIC WAVES

BACKGROUND OF THE INVENTION

1. Field of the Invention

The present invention relates to a method of treating an area of the body by creating a therapeutic combination of materials with ultrasonic waves and spraying the combination onto the area to be treated.

2. Background of the Related Art

When confronted with wounded tissue, physicians and similar practitioners of medical arts have numerous devices and methods at their disposal. For instance, exposing the wound to oxygen may bring about a therapeutic effect. Methods of delivering oxygen to wounds have been developed and are implemented by various devices and compounds. The methods include placing the wound within an oxygen rich environment as to facilitate the diffusion of oxygen from the environment into the wound. Oxygen releasing compounds have also been placed over wounds as to allow for the diffusion of oxygen from the compound into wound.

Administering pharmaceuticals to the wound may also be utilized to treat wounded tissue by providing various therapeutic benefits. For instance, a therapeutic benefit may be obtained by utilizing pharmaceuticals to prevent an infection from developing in the wounded tissue. Specifically, keeping the wound in an infection free state can be accomplished by administering various anti-microbial agents such as, but not limited to, antiseptics, antibiotics, antiviral agents, antifungal agents, or any combination thereof. Administering various growth factors to the wounded tissue may also elicit a therapeutic benefit by promoting the growth of new tissue.

In extreme situations, the practitioner may have to resort to surgery to treat the wounded tissue. Grafting transplanted and/or bioengineered tissue onto the wounded may be necessary with severe wounds.

More experimental treatments, such as exposing the wounded tissue to ultraviolet light, electricity, and/or ultrasound, are also available to the practitioner. For example, U.S. Pat. Nos. 6,478,754, 6,761,729, 6,533,803, 6,569,099, 6,663,554, and 6,960,173 teach methods and devices utilizing an ultrasound generated spray to treat wounded tissues. Methods and devices utilizing indirect contact with the wounded tissue via a liquid aerosol are disclosed in U.S. Pat. Nos. 7,025,735 and 6,916,296.

SUMMARY OF THE INVENTION

Treating severe and/or chronic wounds can be especially difficult. Such wounds are often seen in diabetics, the elderly, individuals with compromised immune systems, and other at risk patient populations. The pain produced by such wounds may disable the patient, thereby reducing the patient's quality of life. An unhealed wound's susceptibility to infection increases a patient's morbidity and mortality. Placing the patient in an environment abundant in drug resistant infectious agents, such as hospital or institutional settings, further increases the patient's morbidity and mortality.

A method of treating areas of the body utilizing ultrasonic vibrations to mix different materials together as to create a therapeutic combination is disclosed. The materials are mixed by passing them through an ultrasound horn, vibrated in resonance, comprising an internal chamber including a back wall, a front wall, and at least one side wall, a radiation surface at the horn's distal end, at least one channel opening into the chamber, and a channel originating in the front wall of the internal chamber and terminating in the radiation surface. As the materials pass through the internal chamber, ultrasonic vibrations emanating from and/or echoing off the various walls of the chamber mix the materials into a potentially therapeutic combination. Ultrasonic vibrations emanating from the radiation surface of the horn may be used to spray the created therapeutic combination onto the area of the body to be treated.

The materials mixed together may include liquids, solids, and/or gases. As the materials pass through chamber they may be mixed by dissolving, suspending, and/or disbursing one material within another material utilized. In the alternative or in combination, the materials may also be mixed in other ways as they pass through the chamber. At least one of the materials may, but need not, be a solvent for at least one of the other materials utilized. Acceptable solvents may include, but are not limited to, water, a saline solution, and/or alcohol. At least one of the materials may, but need not, be a pharmaceutical. Preferably, at least one of the materials should be capable of eliciting a positive therapeutic effect, such as, but not limited to oxygen.

Oxygen is essential for many important aspects of the healing process. For example, oxygen is required for cellular respiration, the process by which cells produce the energy needed to repair the wound. Oxygen is generally supplied to tissues of the body through the body's circulation system. Unfortunately, the blood supply to wounded tissue is often diminished or compromised. Consequently, the amount of oxygen reaching wounded tissue is often reduced. Not only can reduced oxygen levels inhibit the ability of cells to produce energy and/or heal a wound, reduced oxygen levels can lead to the production of an anaerobic environment within the wound favoring the development of certain infections. When treating wounded tissue, oxygen may be indirectly delivered to the tissue via diffusion by placing the wound in an oxygen rich environment or placing an oxygen releasing compound over the wound. However, the epidermis and/or dermis of most animals are not adapted to allow large amounts of oxygen to diffuse into the body. As such, the epidermis and/or dermis may reduce and/or limit the efficacy oxygen rich environments and oxygen releasing compounds in treating wounds.

Ultrasonic vibrations emanating from the radiation surface of an ultrasonically vibrating horn may spray onto a wounded area of the body a solution created by passing oxygen and saline through the horn's internal chamber. Utilizing ultrasonic waves to deliver the solution to the body may allow for the penetration of the solution into and/or across the dermis and/or epidermis. As such, the oxygen within the solution may enter the body, the cells of the dermis and/or epidermis, and/or otherwise become available to wounded tissues. This may increase the ability of the cells within and/or around the wound to carry out cellular respiration, as to produce energy needed in the healing process.

The amount of mixing that occurs within the chamber may be adjusted by changing the locations of the chamber's surfaces with respect to ultrasonic vibrations passing through the horn. When the horn is vibrated in resonance by a transducer attached to its proximal end, vibrations travel from the proximal end to the distal end of the horn. The vibrations can be conceptualized as ultrasonic waves traveling down the length of the horn. As the ultrasonic vibrations travel down the length of the horn, the horn contracts and expands. However, the entire length of the horn is not expanding and contracting. Instead, the segments of the horn between the nodes of the ultrasonic vibrations (points of minimum deflection or amplitude) are expanding and contracting. The portions of the horn lying exactly on the nodes of the ultrasonic vibrations are not expanding and contracting. Therefore, only the segments of the horn between the nodes are expanding and contracting, while the portions of the horn lying exactly on nodes are not moving. It is as if the ultrasound horn has been physically cut into separate pieces. The pieces of the horn corresponding to nodes of the ultrasonic vibrations are held stationary, while the pieces of the horn corresponding to the regions between nodes are expanding and contracting. If the pieces of the horn corresponding to the regions between nodes were cut up into even smaller pieces, the pieces expanding and contracting the most would be the pieces corresponding to the antinodes of the ultrasonic vibrations (points of maximum deflection or amplitude).

Moving forwards and backwards, the back wall of the chamber induces ultrasonic vibrations in at least one of the materials within the chamber. As the back wall moves forward it hits the material. Striking the material, like a mallet hitting a gong, the back wall induces ultrasonic vibrations that travel through the material. The vibrations traveling through the material possess the same frequency as the ultrasonic vibrations traveling through horn. The farther forwards and backwards the back wall of the chamber moves, the more forcefully the back wall strikes the material within the chamber and the higher the amplitude of the ultrasonic vibrations within the material.

When the ultrasonic vibrations traveling through the material within the chamber strike the front wall of the chamber, the front wall compresses forwards. The front wall then rebounds backwards, striking the material within the chamber, and thereby creates an echo of the ultrasonic vibrations that struck the front wall within the material. If the front wall of the chamber is struck by an antinode of the ultrasonic vibrations traveling through chamber, then the front wall will move as far forward and backward as is possible. Consequently, the front wall will strike the material within the chamber more forcefully and thus generate an echo with the largest possible amplitude. If, however, the ultrasonic vibrations passing through the chamber strike the front wall of the chamber at a node, then the front wall will not be forced forward because there is no movement at a node. Consequently, an ultrasonic vibration striking the front wall at a node will not produce an echo.

Positioning the front and back walls of the chamber such that at least one point on both, preferably their centers, lie approximately on antinodes of the ultrasonic vibrations passing through the chamber maximizes the amount of mixing occurring within the chamber. Moving the back wall of the chamber away from an antinode and towards a node decreases the amount of mixing induced by ultrasonic vibrations emanating from the back wall. Likewise, moving the front wall of the chamber away from an antinode and towards a node decreases the amount of mixing induced by ultrasonic vibrations echoing off the front wall. Therefore, positioning the front and back walls of the chamber such that center of both the front and back wall lie approximately on nodes of the ultrasonic vibrations passing through the chamber minimizes the amount of mixing within the chamber.

The amount of mixing that occurs within the chamber can also be adjusted by controlling the volume of the materials within the chamber, especially when one of the materials is a fluid. Ultrasonic vibrations within the chamber may cause atomization of the fluid. As the fluid atomizes, its volume increases which, may cause the fluid to separate from the other material within the chamber. However, if the materials completely fill the chamber, then there is no room in the chamber to accommodate an increase in the volume of the fluid. Consequently, the amount of atomization occurring within the chamber when the chamber is completely filled will be decreased and the amount of mixing increased.

The mixing occurring within the chamber may also be enhanced by including an ultrasonic lens within the front wall of the chamber. Ultrasonic vibrations striking the lens within the front wall of the chamber are directed to reflect back into the chamber in a specific manner depending upon the configuration of the lens. For instance, a lens within the front wall of the chamber may contain a concave portion. Ultrasonic vibrations striking the concave portion of the lens would be reflected towards the side walls. Upon impacting the side walls, the reflected ultrasonic vibrations would be reflected again, and would thus echo throughout the chamber. If the concaved portion or portions within a lens form an overall parabolic configuration in at least two dimensions, then the ultrasonic vibrations echoing off the lens and/or the energy they carry may be focused towards the focus of the parabola.

In combination or in the alternative, the lens within the front wall of the chamber may also contain a convex portion. Again, ultrasonic vibrations emitted from the chamber's back wall striking the lens within the front wall would be directed to reflect back into and echo throughout the chamber in a specific manner. However, instead of being directed towards a focal point as with a concave portion, the ultrasonic vibrations echoing off the convex portion are reflected in a dispersed manner towards the side walls of the chamber. Upon reaching the chamber's side walls, the ultrasonic vibrations reflect off the side walls. If the angle of deflection off the side wall of the chamber is sufficiently great, the ultrasonic vibrations may travel towards and reflect off a different side wall of the chamber. Thus, the inclusion of an ultrasonic lens within the front wall of the chamber containing a convex portion increases the amount of echoing within the chamber. Increasing the amount of echoing, in turn, increases the amount of ultrasonic vibrations agitating, cavitating, and/or colliding against the fluids within the chamber, thereby enhancing the mixing of the fluids within the chamber.

In combination or in the alternative, the back wall of the chamber may also contain an ultrasonic lens possessing concave and/or convex portions. Such portions within the back wall lens of the chamber function similarly to their front wall lens equivalents, except that in addition to directing and/or focusing echoing ultrasonic vibrations, they also direct and/or focus the ultrasonic vibrations as they are emitted into the chamber.

In combination or in the alternative, the mixing occurring within the chamber may also be enhanced by incorporating protrusions on the side walls of the chamber. The protrusions may be formed in a variety of shapes such as, but not limited to, convex, spherical, triangular, rectangular, polygonal, and/or any combination thereof. Emitting ultrasonic vibrations into the chamber from their distal facing edges, the protrusions within the inner chamber may enhance mixing of the materials within the chamber by increasing the amount of ultrasonic vibrations within the chamber. Increasing the surface area of the chamber's side wall, the protrusions may enhance echoing by providing more surfaces from which ultrasonic vibrations can echo.

The protrusions may be discrete elements. Alternatively, the protrusions may be discrete bands encircling the internal chamber. The protrusions may also spiral down the chamber similar to the threading within a nut.

In combination or in the alternative, the mixing occurring within the chamber may be enhanced by placing at least one free member within the chamber. The ultrasonic vibrations within the chamber induce the free member to move about the chamber. The motion of the free member may further mix the materials passing through the chamber. The ultrasonic vibrations within the chamber may push the free member in the direction the ultrasonic vibrations are traveling. As such, the conformation of the lenses within the front and/or back walls of the chamber may influence the motion of the free member about the chamber. If the front or back wall contains an ultrasonic lens with a concave portion or portions that form an overall parabolic configuration in at least two dimensions, the ultrasonic vibrations may converge at the parabola's focus and then diverge as the vibrations travel from one wall towards the opposite wall. As such, the ultrasonic vibrations may induce the free member to travel towards the focus as it moves from one wall towards the opposite wall. If the front and back walls each contain a lens that forms an overall parabolic configuration in at least two dimensions with different foci, then the free member may travel primarily about the foci, consistently moving towards one focus and away from the other. If the parabolas share a common focus, then the free member may travel primarily about the single focus, consistently moving towards and away from it.

If the front or back wall contains a lens with a convex portion, the ultrasonic vibrations may be dispersed throughout the internal chamber. As such, the ultrasonic vibration may induce the free member to travel randomly about the chamber as it moves from one wall towards the opposite wall. Thus, if the front and/or back walls of the chamber contain a lens with a convex portion, then the free member may travel randomly about the chamber as it moves back-and-forth between the front and back wall.

The amount of mixing occurring within the internal chamber may also be controlled by adjusting the amplitude of the ultrasonic vibrations traveling down the length of the horn. Increasing the amplitude of the ultrasonic vibrations may increase the degree to which the materials within the chamber are mixed. If the horn is ultrasonically vibrated in resonance by a piezoelectric transducer driven by an electrical signal supplied by a generator, then increasing the voltage of the electrical signal will increase the amplitude of the ultrasonic vibrations traveling down the horn.

After being mixed, the materials are sprayed onto the area of the body to be treated. The combination of materials may be sprayed onto the body in several manners. For instance, a flowing carrier gas may be utilized to spray the combination onto the body. The combination may also be sprayed onto the body by pressurizing the combination and then expelling it towards the area to be treated. The combination may also be sprayed onto the body by using ultrasonic vibrations emanating from the radiation surface. The enumerated manners of spraying the combination onto the body may be used in combination or in the alternative. Furthermore, other manners of spraying the combination onto the area of the body, readily recognizable to persons of ordinary skill in the art, may be used in addition to and/or in combination with the manners enumerated.

If the combination is sprayed onto an area of the body by utilizing ultrasonic vibrations emanating from the radiation surface, then adjusting the amplitude of the ultrasonic waves traveling down the length of the horn may focus the spray produced at the radiation surface. Creating a focused spray may be accomplished by utilizing the ultrasonic vibrations emanating from the radiation surface to confine and direct the spray pattern. Ultrasonic vibrations emanating from the radiation surface may direct and confine the vast majority of the spray produced within the outer boundaries of the radiation surface. The level of confinement obtained by the ultrasonic vibrations emanating from the radiation surface depends upon the amplitude of the ultrasonic vibrations traveling down the horn. As such, increasing the amplitude of the ultrasonic vibrations passing through the horn may narrow the width of the spray pattern produced; thereby focusing the spray. For instance, if the spray is fanning too wide, increasing the amplitude of the ultrasonic vibrations may narrow the spray pattern. Conversely, if the spray is too narrow, then decreasing the amplitude of the ultrasonic vibrations may widen the spray pattern.

Changing the geometric conformation of the radiation surface may also alter the shape of the spray pattern. Producing a roughly column-like spray pattern may be accomplished by utilizing a radiation surface with a planar face. Generating a spray pattern with a width smaller than the width of the horn may be accomplished by utilizing a tapered radiation surface. Further focusing of the spray may be accomplished by utilizing a concave radiation surface. In such a configuration, ultrasonic waves emanating from the concave radiation surface may focus the spray through the focus of the radiation surface. If it is desirable to focus, or concentrate, the spray produced towards the inner boundaries of the radiation surface, but not towards a specific point, then utilizing a radiation surface with slanted portions facing the central axis of the horn may be desirable. Ultrasonic waves emanating from the slanted portions of the radiation surface may direct the spray inwards, towards the central axis. There may, of course, be instances where a focused spray is not desirable. For instance, it may be desirable to quickly apply the combination to a large area of the body. In such instances, utilizing a convex radiation surface may produce a spray pattern with a width wider than that of the horn. The radiation surface utilized may possess any combination of the above mentioned configurations such as, but not limited to, an outer concave portion encircling an inner convex portion and/or an outer planar portion encompassing an inner conical portion. Inducing resonating vibrations within the horn facilitates the production of the spray patterns described above, but may not be necessary.

It should be noted and appreciated that other benefits and/or mechanisms of operation, in addition to those listed, may be elicited by methods in accordance with the present invention. The mechanisms of operation presented herein are strictly theoretical and are not meant in any way to limit the scope this disclosure and/or the accompanying claims.

BRIEF DESCRIPTION OF THE DRAWINGS

The present invention will be shown and described with reference to the drawings of preferred embodiments and clearly understood in details.

FIG. 1 depicts a flow chart illustrating the method of treating areas of the body utilizing ultrasonic vibrations to create a therapeutic combination by mixing different materials together.

FIG. 2 illustrates an apparatus comprising a horn with an internal chamber that may be utilized to create the therapeutic combination and/or spray it onto an area of the body to be treated.

DETAILED DESCRIPTION OF THE DRAWING

Figure 3:
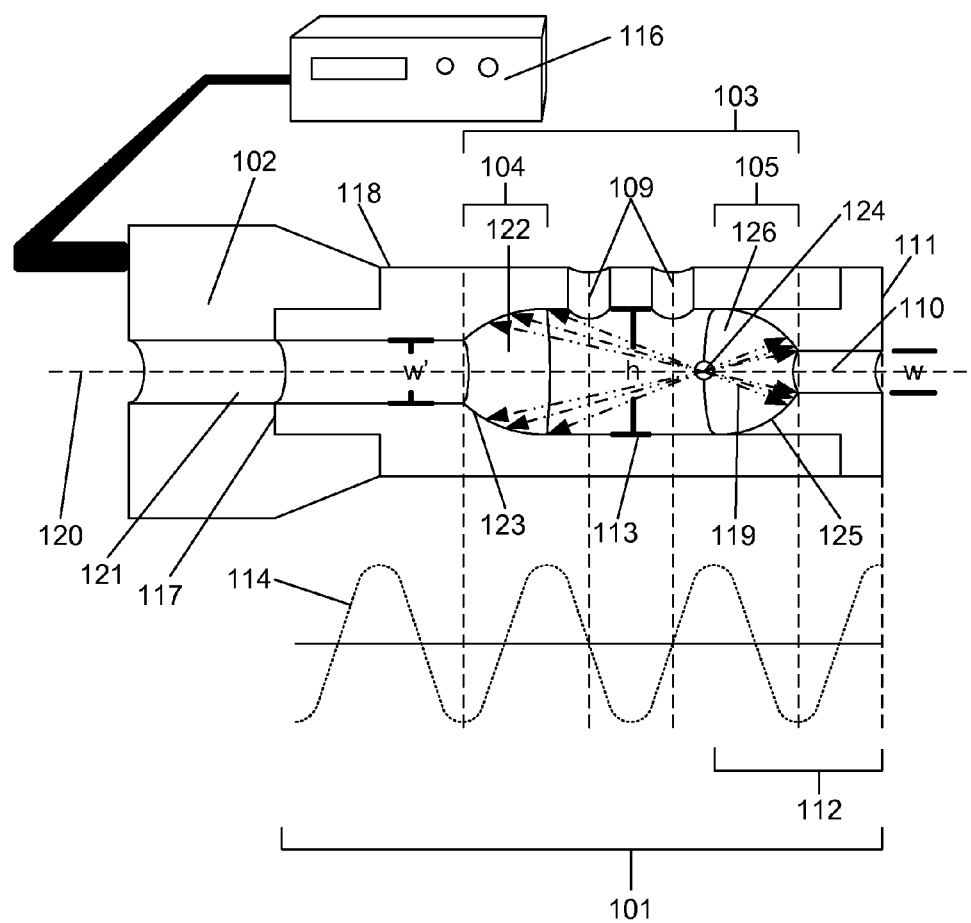
FIG. 3 illustrates an alternative ultrasound horn comprising an internal chamber that may be used to create the therapeutic combination and/or spray it onto the body characterized by ultrasonic vibrations emanating from a lens within the back wall of the chamber echoing off a lens within the front wall of the chamber, and thus being reflected back into chamber.

Preferred embodiments of the method of treating areas of the body utilizing ultrasonic vibrations to create a therapeutic combination by mixing different materials together are illustrated throughout the figures and described in detail below. Those skilled in the art will understand the advantages provided by the treatment method upon review.

The method begins, as depicted by Diamond 1 of FIG. 1, by first selecting the materials to be mixed together to create the therapeutic combination. The materials selected may include liquids, solids, and/or gases. At least one of the materials may, but need not, be a pharmaceutical. Preferably, at least one of the materials should be capable of eliciting a positive therapeutic effect. At least one of the materials may, but need not, be a solvent for at least one of the other materials utilized. Any solvent not unnecessarily toxic to the area of the body to be treated may be used such as, but not limited to, saline, alcohol, water, or any combination thereof. Those skilled in the medical arts will be able to recognize the appropriate materials to be combined to create the therapeutic combination upon examination and/or diagnosis of the area to be treated.

The selected materials are then mixed by passing them through an ultrasound horn, vibrating in resonance at a frequency of approximately 16 kHz or greater, as depicted by Box 2. Preferably, the horn through which the materials pass comprises an internal chamber including a back wall, a front wall, and at least one side wall, a radiation surface at the horn's distal end, at least one channel opening into the chamber, and a channel originating in the front wall of the internal chamber and terminating in the radiation surface. Acceptable horns are described in U.S. patent application Ser. No. 11/777,934, filed Jul. 13, 2007, and Ser. No. 11/777,955, filed Jul. 13, 2007, the teachings of which are hereby incorporated by reference and briefly reiterated in part below.

As the materials pass through the internal chamber of the horn, they are mixed by ultrasonic vibrations emanating from and/or echoing off the various surfaces of the chamber, as to create a therapeutic combination, as depicted by Box 4. The mixing of the materials within the chamber can be enhanced by placing at least one free member within the chamber before passing the materials through the chamber, as depicted by Box 3 of FIG. 1. Ultrasonic vibrations within the chamber strike the free member causing it to move about chamber and physically mix the materials. In combination or in the alternative to physically mixing the materials, the free member may also reflect ultrasonic vibrations striking it. Thus, as the free member moves about the chamber it may reflect the ultrasonic vibrations striking it in random directions. The free members, therefore, may create random echoing of the ultrasonic vibrations within the chamber that may further increase the mixing of the materials.

In keeping with FIG. 1, the material passing through the chamber may be simultaneously mixed and atomized by the ultrasonic vibrations within the chamber, as to create an atomized therapeutic combination. The simultaneous mixing and atomization of the material, if desired, can be accomplished by leaving a gas filled space within the chamber, as depicted by Box 5. The amount of atomization occurring within the chamber during the creation of the therapeutic combination can be adjusted by controlling the volume of solid and/or liquid materials within the chamber. Atomization of at least one of materials passing through the chamber, especially liquids, causes the volume of the combination to increase, by necessity. However, if liquid and/or solid materials completely fill the chamber, then there is no room in the chamber to accommodate an increase in the volume of the combination. Consequently, the amount of atomization occurring within the chamber when the chamber is completely filled with liquid and/or solid materials will be significantly decreased and the amount of mixing may be significantly increased.

In keeping with FIG. 1, if an atomized combination is desired, and the therapeutic combination is not sufficiently atomized during its creation, then it should be further atomized, as depicted by Box 6. The combination may be atomized by its passage through the channel originating in the front wall of the internal chamber and terminating in the horn's radiation surface. In the alternative or in combination, the combination of materials exiting the horn may be atomized by ultrasonic vibrations emanating from the radiation surface. The enumerated manners of atomizing the combination may be used in combination or in the alternative. Furthermore, other manners of atomizing the combination, which are readily recognizable to those of ordinary skill in the art, may be utilized in addition to and/or in combination with the enumerated manners.

After mixing the materials passing through the chamber and, if desired, atomizing the combination created, the therapeutic combination should then be sprayed onto the area of the body to be treated, as depicted by Box 7. The combination may be sprayed onto the body in several manners. For instance, a flowing carrier gas may be utilized to spray the combination. The combination may also be sprayed by pressurizing the combination and then expelling it towards the body. The combination may also be sprayed onto the body by using ultrasonic vibrations emanating from the radiation surface. The enumerated manners of spraying the combination onto the body may be used in combination or in the alternative. Furthermore, other manners of spraying the combination onto the area of the body, which are readily recognizable to those of ordinary skill in the art, may be utilized in addition to and/or in combination with the enumerated manners.

If the created combination is to be used to treat a wound, it should be sprayed onto the wound for approximately five seconds or longer, at least once daily until healed. However, more severe wounds may require more frequent treatments and/or longer treatment sessions.

FIG. 2 illustrates an apparatus that may be utilized to create the therapeutic combination and/or spray it onto an area of the body to be treated. The apparatus comprises a horn 101 and an ultrasound transducer 102 attached to the proximal surface 117 of horn 101 powered by generator 116. As ultrasound transducers and generators are well known in the art they need not and will not, for the sake of brevity, be described in detail herein. Ultrasound horn 101 comprises a proximal surface 117, a radiation surface 111 opposite proximal end 117, and at least one radial surface 118 extending between proximal surface 117 and radiation surface 111. Within horn 101 is an internal chamber 103 containing a back wall 104, a front wall 105, at least one side wall 113 extending between back wall 104 and front wall 105, and an ultrasonic lens 122 within back wall 104. As to induce vibrations within horn 101, ultrasound transducer 102 may be mechanically coupled to proximal surface 117. Mechanically coupling horn 101 to transducer 102 may be achieved by mechanically attaching (for example, securing with a threaded connection), adhesively attaching, and/or welding horn 101 to transducer 102. Other means of mechanically coupling horn 101 and transducer 102, readily recognizable to persons of ordinary skill in the art, may be used in combination with or in the alternative to the previously enumerated means. Alternatively, horn 101 and transducer 102 may be a single piece. When transducer 102 is mechanically coupled to horn 101, driving transducer 102 with an electrical signal supplied from generator 116 induces ultrasonic vibrations 114 within horn 101. If transducer 102 is a piezoelectric transducer, then the amplitude of the ultrasonic vibrations 114 traveling down the length of horn 101 may be increased by increasing the voltage of the electrical signal driving transducer 102.

As the ultrasonic vibrations 114 travel down the length of horn 101, back wall 104 oscillates back-and-forth. The back-and-forth movement of back wall 104 induces the release ultrasonic vibrations from lens 122 into the materials inside chamber 103. Positioning back wall 104 such that at least one point on lens 122 lies approximately on an antinode of the ultrasonic vibrations 114 passing through horn 101 may maximize the amount and/or amplitude of the ultrasonic vibrations emitted into the materials in chamber 103. Preferably, the center of lens 122 lies approximately on an antinode of the ultrasonic vibrations 114. The ultrasonic vibrations emanating from lens 122, represented by arrows 119, travel towards the front of chamber 103. As to minimize the oscillations and/or vibrations of front wall 105, it may be desirable to position front wall 105 such that at least one point on front wall 105 lies on a node of the ultrasonic vibrations 114. Preferably, the center of front wall 105 lies approximately on a node of the ultrasonic vibrations 114.

The specific lens illustrated in FIG. 2A contains a concave portion 123. If concave portion 123 forms an overall parabolic configuration in at least two dimensions, then the ultrasonic vibrations, depicted by arrows 119, emanating from concave portion 123 of lens 122 travel in an undisturbed pattern of convergence towards the parabola's focus 124. As the ultrasonic vibrations 119 converge at focus 124, the ultrasonic energy carried by vibrations 119 may become focused at focus 124. The materials passing through chamber 103 are therefore exposed to the greatest concentration of ultrasonic energy at focus 124. Consequently, the ultrasonically induced mixing of the materials may be greatest at focus 124. Positioning focus 124 at or near the opening of channel 110, as to be in close proximity to the opening of channel 110 in front wall 105 may, therefore, yield the maximum mixing of the materials as the materials enters channel 110.

The materials to be atomized and/or mixed enter chamber 103 of the embodiment depicted in FIG. 1 through at least one channel 109 originating in radial surface 118 and opening into chamber 103. Preferably, channel 109 encompasses a node of the ultrasonic vibrations 114 traveling down the length of the horn 101 and/or emanating from lens 122. In the alternative or in combination, channel 109 may originate in radial surface 118 and open at back wall 104 into chamber 103. Upon exiting channel 109, the materials pass through chamber 103. The combined materials then exit chamber 103 through channel 110, originating within front wall 105 and terminating within radiation surface 111. If the combination is primarily a fluid, the pressure of the combination decreases while its velocity increases as it passes through channel 110. Thus, as the combination flows through channel 110, the pressure acting on the combination may be converted to kinetic energy. If the combinations gains sufficient kinetic energy as it passes through channel 110, then the attractive forces between the molecules of the combination may be broken, causing the combination to atomize as it exits channel 110 at radiation surface 111. If the combination exiting horn 101 is to be atomized by the kinetic energy gained from its passage through channel 110, then the maximum height (h) of chamber 103 should be larger than maximum width (w) of channel 110. Preferably, the maximum height of chamber 103 should be approximately 200 times larger than the maximum width of channel 110 or greater.

It is preferable if at least one point on radiation surface 111 lies approximately on an antinode of the ultrasonic vibrations 114 passing through horn 101.

As to simplify manufacturing, ultrasound horn 101 may further comprise cap 112 attached to its distal end. Cap 112 may be mechanically attached (for example, secured with a threaded connector), adhesively attached, and/or welded to the distal end of horn 101. Comprising front wall 105, channel 110, and radiation surface 111, a removable cap 112 permits the level of atomization and/or the spray pattern produced to be adjusted depending on need and/or circumstances. For instance, the width of channel 110 may need to be adjusted to produce the desired level of atomization with different combinations. The geometrical configuration of the radiation surface may also need to be changed as to create the appropriate spray pattern for different applications. Attaching cap 112 to the present invention at approximately a nodal point of the ultrasonic vibrations 114 passing through horn 101 may help prevent the separation of cap 112 from horn 101 during operation.

Alternative embodiments of an ultrasound horn 101 that may be utilized to create the therapeutic combination and/or spray it onto the body may possess a single channel 109 opening within side wall 113 of chamber 103. If multiple channels 109 are utilized, they may be aligned along the central axis 120 of horn 101, as depicted in FIG. 2A. Alternatively or in combination, channels 109 may be located on different platans, as depicted in FIG. 2A, and/or the same platan, as depicted in FIG. 2B.

Alternatively or in combination, the materials to be combined may enter chamber 103 through a channel 121 originating in proximal surface 117 and opening within back wall 104, as depicted in FIG. 2. If the combination is to be atomized by its passage through the horn, then the maximum width (w') of channel 121 should be smaller than the maximum height of chamber 103. Preferably, the maximum height of chamber 103 should be approximately twenty times larger than the maximum width of channel 121.

A single channel may be used to deliver the materials to be combined into chamber 103.

FIG. 3 illustrates an alternative ultrasound horn 101 that may be used to create the therapeutic combination and/or spray it onto the body characterized by ultrasonic vibrations 119 emanating from lens 122 echoing off lens 126 within front wall 105, and thus being reflected back into chamber 103. After striking the concave portion 125 of lens 126 within front wall 105, ultrasonic vibrations 119 are reflected back into chamber 103. If concave portion 125 forms an overall parabolic configuration in at least two dimensions, the ultrasonic vibrations 119 echoing backing into chamber 103 may travel in an undisturbed pattern of convergence towards the parabola's focus. The ultrasonic energy carried by the echoing vibrations may become focused at the focus of the parabola formed by the concave portion 125. Converging as they travel towards front wall 105 and then again as they echo back towards back wall 104, ultrasonic vibrations 119 travel back and forth through chamber 103 in an undisturbed, converging echoing pattern.

In the embodiment illustrated in FIG. 3 the parabolas formed by concave portions 123 and 125 have a common focus 124. In the alternative, the parabolas may have a different focus. However, by sharing a common focus 124, the ultrasonic vibrations 119 emanating and/or echoing off the parabolas and/or the energy the vibrations carry may become focused at focus 124. The materials passing through chamber 103 are therefore exposed to the greatest concentration of the ultrasonic agitation, cavitation, and/or energy at focus 124. Consequently, the ultrasonically induced mixing of the materials is greatest at focus 124. Positioning focus 124, or any other focus of a parabola formed by the concave portions 123 and/or 125, at point downstream of the entry of at least two materials into chamber 103 may maximize the mixing of the materials entering chamber 103 upstream of the focus.

The lens within the front and/or back wall of the chamber may contain convex portions. Ultrasonic vibrations emanating from convex portions of the lens within the back wall chamber may travel in an undisturbed dispersed reflecting pattern towards the front wall in the following manner: The ultrasonic vibrations would first be directed towards a side wall of the chamber at varying angles of trajectory. The ultrasonic vibrations would then reflect off the side wall. Depending upon the angle at which the ultrasonic vibrations strike the side wall, they may be reflected through the central axis of the chamber and travel in an undisturbed reflecting pattern towards the front wall. However, if the vibrations emanating from the lens within the back wall strike a side wall at a sufficiently shallow angle, they may be reflected directly towards the front wall, without passing through the central axis. Likewise, when the ultrasonic vibrations strike the convex portions of the lens within the front wall, they may echo back into chamber in an undisturbed dispersed reflecting pattern towards the back wall. As such, some of the ultrasonic vibrations echoing off the lens within the front wall may pass through the central axis after striking a side wall. Some of the echoing ultrasonic vibrations may travel directly towards the back wall after striking a side wall without passing through the central axis. Failing to converge at a single point, or along a single axis, as they travel towards the front wall and then again as they echo back towards the back wall, the ultrasonic vibrations would travel back and forth through the chamber in an undisturbed, dispersed echoing pattern. Consequently, the ultrasonically induced mixing of the materials passing through the chamber may be dispersed throughout the chamber.

It should be appreciated that the configuration of the chamber's front wall lens need not match the configuration of the chamber's back wall lens. Furthermore, the lenses within the front and/or back wall of the chamber may comprise any combination of the above mentioned configurations such as, but not limited to, an outer concave portion encircling an inner convex portion.

Figure 4:
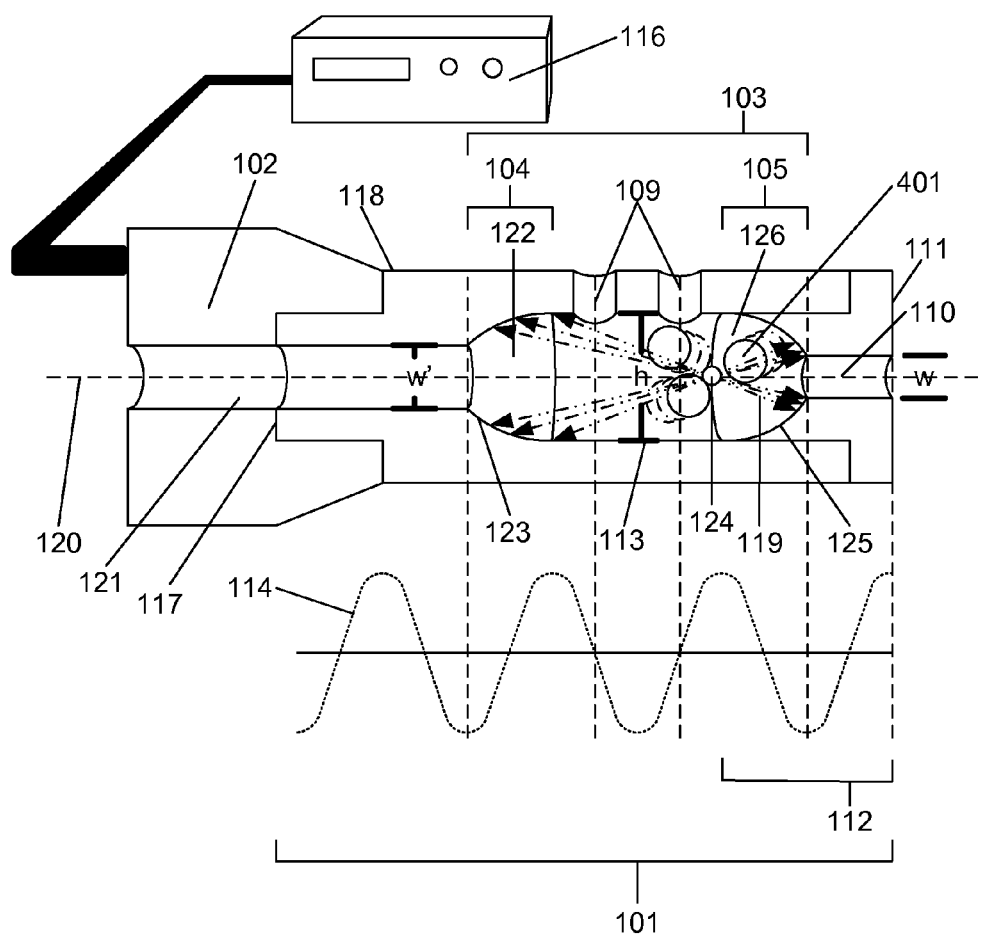
FIG. 4 illustrates an alternative ultrasound horn comprising an internal chamber that may be used to create the therapeutic combination and/or spray it onto the body characterized by at least one free member within the chamber.

FIG. 4 illustrates an alternative ultrasound horn 101 that may be used to create the therapeutic combination and/or spray it onto the body characterized by at least one free member 401 within chamber 103. Ultrasonic vibrations 119 emanating from lens 122 within back wall 104 and/or echoing off lens 126 within front wall 105 may induce free members 401 to move about chamber 103. Traveling through chamber 103, ultrasonic vibrations 119 strike free members 401 and push them in the direction of vibrations 119. As free members 127 move about chamber 103 they mechanically agitate the materials within chamber causing the materials to mix.

In the embodiment illustrated in FIG. 4 the parabolas formed by concave portions of lens 122 and 126 have a common focus 124. In the alternative, the parabolas may have different foci. However, by sharing a common focus 124, the ultrasonic vibrations 119 emanating and/or echoing off the parabolas and/or the energy the vibrations carry may become focused at focus 124. The materials passing through chamber 103 are therefore exposed to the greatest concentration of the ultrasonic agitation, cavitation, and/or energy at focus 124. Furthermore because the parabolas share a common focus, free members 401 may travel primarily about focus 124, consistently moving towards and away from it. Consequently, the ultrasonic induced mixing of the materials is greatest at and/or about focus 124. Positioning focus 124, or any other focus of a parabola formed by the concave portions 123 and/or 125, at point downstream of the entry of at least two materials into chamber 103 may maximize the mixing of the fluids entering chamber 103 upstream of the focus.

Though the specific embodiment of the free members depicted in FIG. 4 are spherical, other geometric configurations are equally possible such as, but not limited to, cylindrical, pyramidal, rectangular, polygonal, or any combination thereof. Furthermore, instead of using three free members as depicted, any number of mixing members may be used. As to prevent the free members from exiting the internal chamber of the horn, it may be desirable to use free members incapable of passing through the channels leading into and/or out of the internal chamber. In the alternative or in combination, screens, meshes, gates, and/or similar structures may be used to prevent the passage of the free members into and/or through the channels within the horn. Preferably, the free members are constructed from a material that is not completely transparent to ultrasonic vibrations.

If the lenses within the front and/or back wall of the chamber contain a convex portion the free members may travel randomly about the chamber as they move back-and-forth between front wall and back wall. Consequently, the overall mixing of the materials passing through the chamber may be dispersed throughout the chamber.

Figure 5:
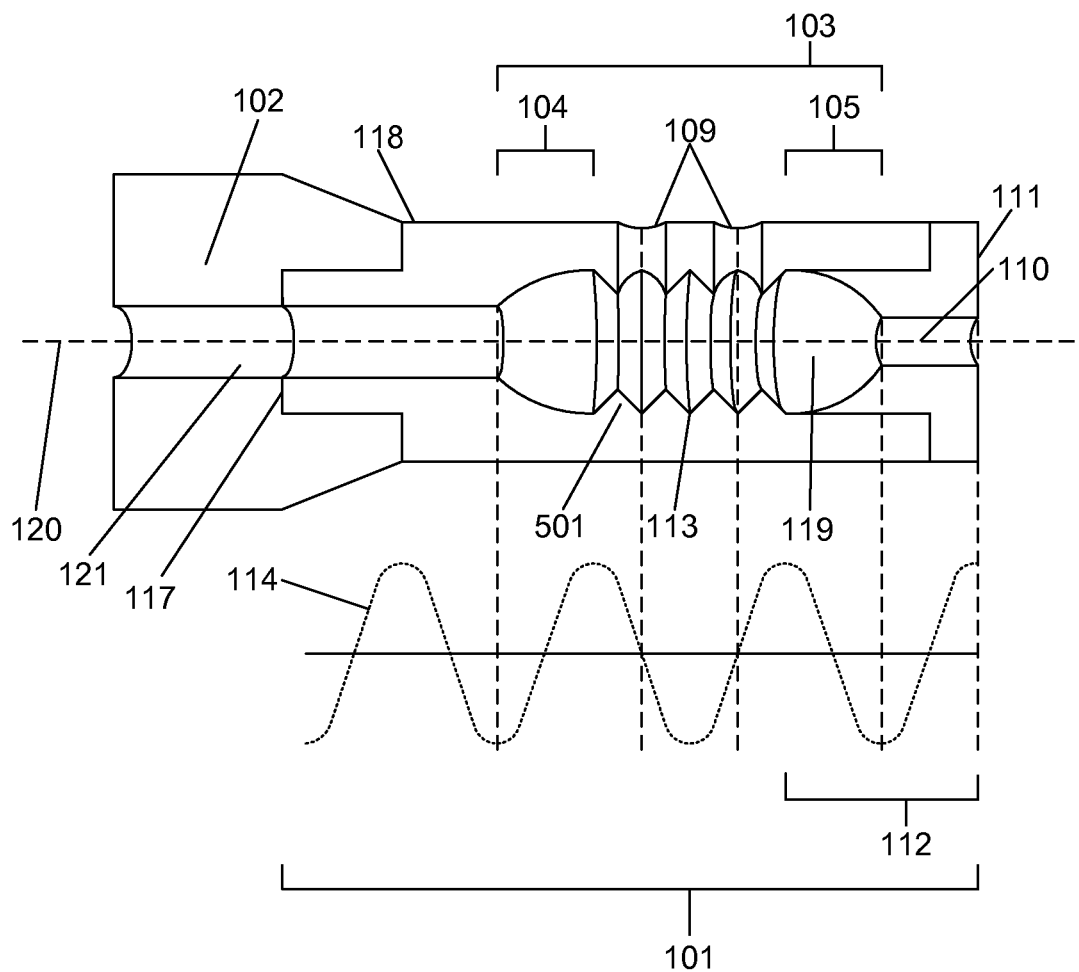
FIG. 5 illustrates an alternative ultrasound horn comprising an internal chamber that may be used to create the therapeutic combination and/or spray it onto the body characterized by at least one protrusion on a side wall of the chamber.

FIG. 5 illustrates an alternative ultrasound horn 101 that may be used to create the therapeutic combination and/or spray it onto the body characterized by at least one protrusion 501 on the side wall 113 and extending into chamber 103. The incorporation of protrusions 501 may enhance ultrasonic echoing within chamber 103 by increasing the amount of ultrasonic vibrations emitted into chamber 103 and/or by providing a larger surface area from which ultrasonic vibrations echo. The distal, or front facing, edges of protrusions 501 may emit ultrasonic waves into the chamber when horn 101 is vibrated. The proximal, or rear facing, and front facing edges of protrusions 501 reflect ultrasonic waves striking the protrusions 501. Emitting and/or reflecting ultrasonic vibrations into chamber 103, protrusions 501 increase the complexity of the echoing pattern of the ultrasonic vibrations within chamber 103. The specific protrusions 501 depicted in FIG. 5 comprise a triangular shape and encircle the cavity. The protrusions may be formed in a variety of shapes such as, but not limited to, convex, spherical, triangular, rectangular, polygonal, and/or any combination thereof. In the alternative or in combination to being a band encircling the chamber, the protrusion may spiral down the chamber similar to the threading within a nut. In combination or in the alternative, the protrusions may be discrete elements secured to a side wall of chamber that do not encircle the chamber. In the alternative or in combination, the protrusions may be integral with side wall or walls of the chamber. Furthermore, protrusions 501 may be utilized to increase mixing within chambers containing convex and/or concave ultrasonic lenses within their front and/or back walls. In the alternative or in combination, protrusions 501 may be utilized to increase mixing within chambers lacking ultrasonic lenses within their front and/or back walls.

Figure 6:
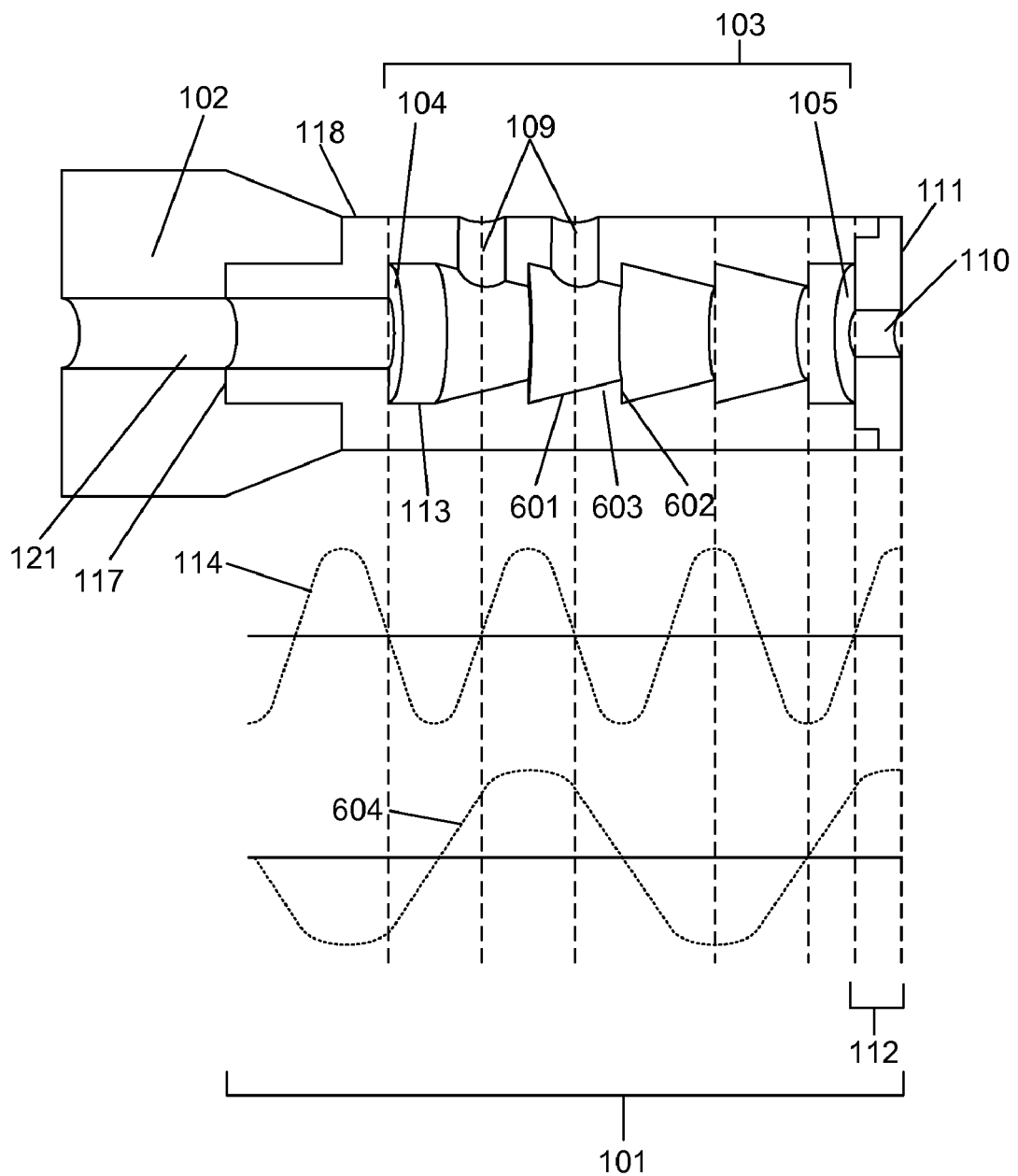
FIG. 6 illustrates an alternative ultrasound horn comprising an internal chamber that may be used to create the therapeutic combination and/or spray it onto the body characterized by at least one protrusion on a side wall and extending into chamber comprising a back facing edge and a front facing edge less streamlined than the back facing edge.

FIG. 6 illustrates an alternative ultrasound horn 101 that may be used to create the therapeutic combination and/or spray it onto the body characterized by at least one protrusion 603 on the side wall 113 and extending into chamber 103 comprising a back facing edge 601 and a front facing edge 602 less streamlined than the back facing edge. As with the embodiment depicted in FIG. 5, the incorporation of protrusions 603 may enhance ultrasonic echoing within chamber 103 by increasing the amount of ultrasonic vibrations emitted into chamber 103 and/or by providing a larger surface area from which ultrasonic vibrations echo. In combination or in the alternative, protrusions 603 may generate a pumping action when horn 101 is vibrated in resonance. As previously stated, vibrating horn 101 in resonance induces segments of the horn to expand and contract as ultrasonic vibrations 114 travel down the length of the horn. As horn 101 expands, the less streamlined front facing edges 602 move forward. As the front facing edges 602 move forward, they push the materials within chamber 103 towards channel 110. Likewise, when the horn contracts, the more streamlined rear facing edges 601 push the material away form channel 110. However, because the rear facing edges 601 are more streamlined then edges 602, more fluid is pushed forwards then backwards. Consequently, an overall forward pumping action is produced by the expansion and contraction of protrusions 603.

As to maximize the movement of front facing edges 602 and pumping action generated, it may be desirable to position front facing edge 602 such that at least one point on the edge lies approximately on an antinode of the ultrasonic vibrations 114 passing through horn 101. Positioning edges 602 on the antinodes of the ultrasonic vibrations passing through horn 101 may also enable the pumping action to be controlled by the frequency of the ultrasonic vibrations. Reducing the frequency of the ultrasonic vibrations passing through horn 101 by one-half, as depicted by vibration 604, may result in half of the edges 602 lying on nodes of the vibration 604. Because there is no movement at a node, the edges 602 lying on the nodes no longer move forward when horn 101 is vibrated. Consequently the edges 602 falling on the nodes no longer contribute to the pumping action produced by the expansion and contraction of horn 101. Reducing the number of edges 602 contributing to the pumping produced, reduces the overall force pushing the material within chamber 103 towards channel 110. Consequently, the material passing through the horn 101 may be expelled from channel 110 less forcefully when frequency of the ultrasonic vibrations passing through horn 101 is reduced.

The pumping action may also be controlled by adjusting the amplitude of the ultrasonic vibrations traveling through horn 101. Increasing the amplitude of the vibrations increases the forward movement of edges 602 and the volume of fluid moved forwards. This may result in an increase in the overall force pushing the material within chamber 103 towards channel 110. Consequently, the material passing through the horn 101 may be expelled from channel 110 more forcefully when the amplitude of the ultrasonic vibrations passing through horn 101 is increased.

Figure 7A:
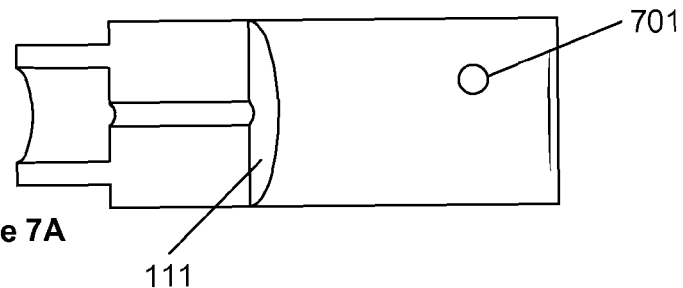
FIG. 7 illustrates alternative embodiments of the radiation surface
Figure 7B:
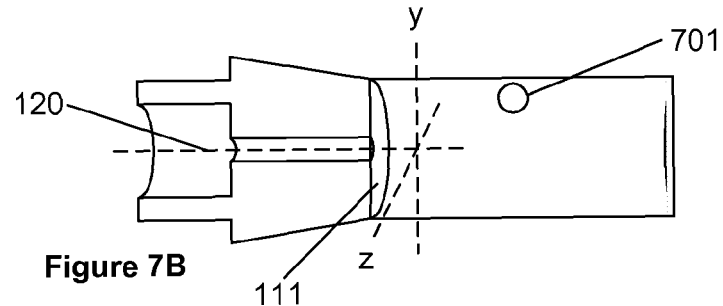

Regardless of the specific horn utilized, ultrasonic vibrations emanating from the horn's radiation surface may atomize the combination exiting the horn into a spray. The ultrasonic vibrations may also direct and/or confine the spray. The manner in which ultrasonic vibrations emanating from the radiation surface direct the spray ejected from the horn utilized depends largely upon the conformation of radiation surface 111. FIG. 7 illustrates alternative embodiments of the radiation surface. FIGS. 7A and 7B depict radiation surfaces 111 comprising a planar face producing a roughly column-like spray pattern. Radiation surface 111 may be tapered such that it is narrower than the width of the horn in at least one dimension oriented orthogonal to the central axis 120 of the horn, as depicted FIG. 7B. Ultrasonic vibrations emanating from the radiation surfaces 111 depicted in FIGS. 7A and 7B may direct and confine the vast majority of spray 701 ejected from channel 110 to the outer boundaries of the radiation surfaces 111. Consequently, the majority of spray 701 emitted from channel 110 in FIGS. 7A and 7B is initially confined to the geometric boundaries of the respective radiation surfaces.

Figure 7C:
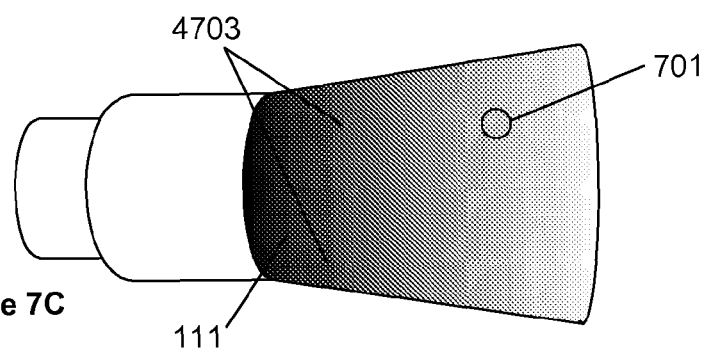
Figure 7D:
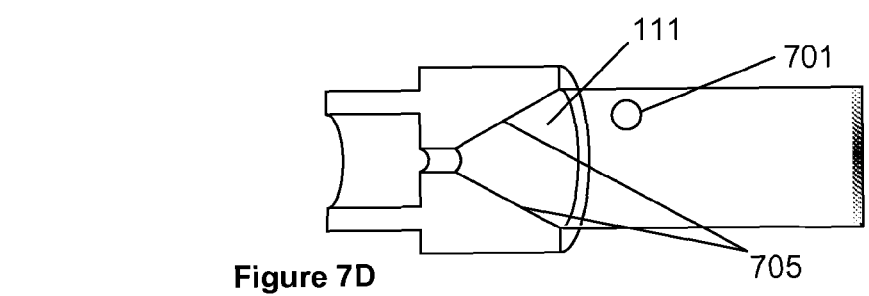
Figure 7E:
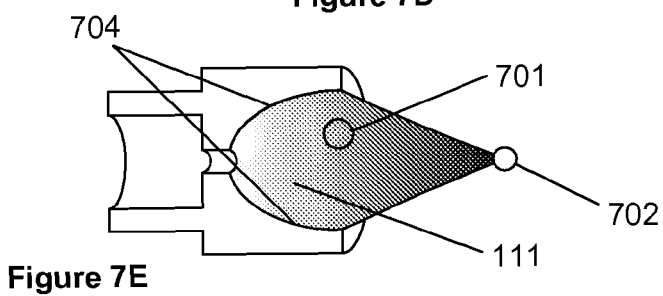

The ultrasonic vibrations emitted from the convex portion 703 of the radiation surface 111 depicted in FIG. 7C directs spray 701 radially and longitudinally away from radiation surface 111. Conversely, the ultrasonic vibrations emanating from the concave portion 704 of the radiation surface 111 depicted in FIG. 7E focuses spray 701 through focus 702. Maximizing the focusing of spray 701 towards focus 702 may be accomplished by constructing radiation surface 111 such that focus 702 is the focus of an overall parabolic configuration formed in at least two dimensions by concave portion 704. The radiation surface 111 may also possess a conical portion 705 as depicted in FIG. 7D. Ultrasonic vibrations emanating from the conical portion 705 direct the atomized spray 701 inwards. The radiation surface may possess any combination of the above mentioned configurations such as, but not limited to, an outer concave portion encircling an inner convex portion and/or an outer planar portion encompassing an inner conical portion.

Regardless of the configuration of the radiation surface, adjusting the amplitude of the ultrasonic vibrations traveling down the length of the horn utilized may be useful in focusing the spray exiting the horn. The level of confinement obtained by the ultrasonic vibrations emanating from the radiation surface and/or the ultrasonic energy the vibrations carry depends upon the amplitude of the ultrasonic vibrations traveling down horn. As such, increasing the amplitude of the ultrasonic vibrations may narrow the width of the spray pattern produced; thereby focusing the spray produced. For instance, if the spray exceeds the geometric bounds of the radiation surface, i.e. is fanning too wide, increasing the amplitude of the ultrasonic vibrations may narrow the spray. Conversely, if the spray is too narrow, then decreasing the amplitude of the ultrasonic vibrations may widen the spray. If the horn is vibrated in resonance frequency by a piezoelectric transducer attached to its proximal end, increasing the amplitude of the ultrasonic vibrations traveling down the length of the horn may be accomplished by increasing the voltage of the electrical signal driving the transducer.

The horn utilized may be capable of vibrating in resonance at a frequency of approximately 16 kHz or greater. The ultrasonic vibrations traveling down the horn may have an amplitude of approximately 1 micron or greater. It is preferred that the horn utilized be capable of vibrating in resonance at a frequency between approximately 20 kHz and approximately 200 kHz. It is recommended that the horn be capable of vibrating in resonance at a frequency of approximately 30 kHz.

The signal driving the ultrasound transducer may be a sinusoidal wave, square wave, triangular wave, trapezoidal wave, or any combination thereof.

It should be appreciated that elements described with singular articles such as "a", "an", and/or "the" and/or otherwise described singularly may be used in plurality. It should also be appreciated that elements described in plurality may be used singularly.

Although specific embodiments of apparatuses and methods have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive. Combinations of the above embodiments and other embodiments as well as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. A method comprising the steps of:

a. vibrating an ultrasonic horn in resonance at a frequency of approximately 16 kHz or greater comprising:
   i. a proximal surface;
   ii. a radiation surface;
   iii. at least one radial surface extending between the proximal end and the radiation surface;
   iv. an internal chamber containing:
      1. a back wall;
      2. a front wall;
      3. at least one side wall extending between the back wall and the front wall; and
      4. an ultrasonic lens within the back wall;
   v. at least one channel originating in a surface other than the radiation surface and opening into the internal chamber; and
   vi. a channel originating in the front wall of the internal chamber and terminating in the radiation surface;
b. passing at least two different materials through the chamber;
c. mixing the materials passing through the chamber with ultrasonic vibrations eminating from the lens within the back wall of the chamber; and
d. spraying the materials onto an area of the body.

2. The method of claim 1 characterized by at least one of the materials passing through the chamber being a solvent for at least one of the other materials.

3. The method of claim 1 characterized by a saline solution being at least one of the materials passed through chamber.

4. The method of claim 1 characterized by a pharmaceutical being at least one of the materials passed through the chamber.

5. The method of claim 1 characterized by oxygen being at least one of the materials passed through the chamber.

6. The method of claim 1 further comprising the step of allowing the vibrations emanating from the back wall to echo off an ultrasonic lens within the front wall of the chamber.

7. The method of claim 6 further comprising the step of mixing the materials passing through the chamber with the ultrasonic vibrations echoing off the lens within the front wall of the chamber.

8. The method of claim 1 further comprising the step of allowing vibrations to emanate from the radiation surface.

9. The method of claim 8 characterized by the materials being sprayed onto the body by the vibrations emanating from the radiation surface.

10. A method comprising the steps of:

a. vibrating an ultrasonic horn in resonance at a frequency of approximately 16 kHz or greater comprising:
   i. a proximal surface;
   ii. a radiation surface;
   iii. at least one radial surface extending between the proximal end and the radiation surface;
   iv. an internal chamber containing:
      1. a back wall;
      2. a front wall;
      3. at least one side wall extending between the back wall and the front wall; and
      4. an ultrasonic lens within the back wall;
   v. at least one channel originating in a surface other than the radiation surface and opening into the internal chamber;
   vi. a channel originating in the front wall of the internal chamber and terminating in the radiation surface; and
   vii. at least one free member within the chamber.
b. passing at least two different materials through the chamber;
c. mixing the materials passing through the chamber with ultrasonic vibrations emanating from the lens within the back wall of the chamber; and
d. spraying the materials onto an area of the body.

11. The method of claim 10 characterized by at least one of the materials passing through the chamber being a solvent for at least one of the other materials.

12. The method of claim 10 characterized by a saline solution being at least one of the materials passed through chamber.

13. The method of claim 10 characterized by a pharmaceutical being at least one of the materials passed through the chamber.

14. The method of claim 10 characterized by oxygen being at least one of the materials passed through the chamber.

15. The method of claim 10 further comprising the step of allowing the vibrations emanating from the back wall to echo off the free member.

16. The method of claim 15 further comprising the step of mixing the materials passing through the chamber with the ultrasonic vibrations echoing off the free member.

17. The method of claim 10 further comprising the step of inducing the free member to move about the chamber by striking the free member with the vibrations emanating from the back wall.

18. The method of claim 17 further comprising the step of mixing the materials passing through the chamber with the movement of the free member.

19. The method of claim 10 further comprising the step of allowing vibrations to emanate from the radiation surface.

20. The method of claim 19 characterized by the materials being sprayed onto the body by the vibrations emanating from the radiation surface.

* * * * *